United States Patent
Akirav

(10) Patent No.: US 9,127,317 B2
(45) Date of Patent: Sep. 8, 2015

(54) METHOD FOR USING PROBE BASED PCR DETECTION TO MEASURE THE LEVELS OF CIRCULATING DEMETHYLATED β CELL DERIVED DNA AS A MEASURE OF β CELL LOSS IN DIABETES

(71) Applicant: Winthrop-University Hospital, Mineola, NY (US)

(72) Inventor: Eitan Moshe Akirav, Plainview, NY (US)

(73) Assignee: Winthrop-University Hospital, Mineola, NY (US)

( * ) Notice: Subject to any disclaimer, the term of this patent is extended or adjusted under 35 U.S.C. 154(b) by 3 days.

(21) Appl. No.: 13/784,017

(22) Filed: Mar. 4, 2013

(65) Prior Publication Data

US 2013/0230850 A1 Sep. 5, 2013

Related U.S. Application Data

(60) Provisional application No. 61/606,140, filed on Mar. 2, 2012.

(51) Int. Cl.
  C12Q 1/68 (2006.01)
(52) U.S. Cl.
  CPC ........ *C12Q 1/6883* (2013.01); *C12Q 2600/154* (2013.01); *C12Q 2600/158* (2013.01)
(58) Field of Classification Search
  CPC ....................................................... C12Q 1/68
  USPC ....................................................... 435/6.11
  See application file for complete search history.

(56) References Cited

U.S. PATENT DOCUMENTS

| | | | |
|---|---|---|---|
| 4,935,342 A | 6/1990 | Seligson et al. |
| 5,057,426 A | 10/1991 | Henco et al. |
| 5,234,809 A | 8/1993 | Boom et al. |
| 5,405,951 A | 4/1995 | Woodard |
| 5,990,301 A | 11/1999 | Colpan et al. |
| 6,020,124 A | 2/2000 | Sorenson |
| 6,103,476 A | 8/2000 | Tyagi et al. |
| 6,150,097 A | 11/2000 | Tyagi et al. |
| 6,214,979 B1 | 4/2001 | Gelfand et al. |
| 6,485,901 B1 | 11/2002 | Gildea et al. |
| 6,485,903 B1 | 11/2002 | Mayrand |
| 6,548,254 B2 | 4/2003 | Beckman et al. |
| 6,649,349 B2 | 11/2003 | Gildea et al. |
| 6,680,377 B1 | 1/2004 | Stanton et al. |
| 6,811,973 B1 | 11/2004 | Reich |
| 7,005,265 B1 | 2/2006 | Fan et al. |
| 7,015,317 B2 | 3/2006 | Mullen et al. |
| 7,070,933 B2 | 7/2006 | Browne |
| 7,081,336 B2 | 7/2006 | Bao et al. |
| 7,153,654 B2 | 12/2006 | Wei et al. |
| 7,183,052 B2 | 2/2007 | Sorge |
| 7,241,596 B2 | 7/2007 | Mayrand |
| 7,271,265 B2 | 9/2007 | Haugland et al. |
| 7,399,591 B2 | 7/2008 | Bao et al. |
| 7,413,708 B2 | 8/2008 | Mayrand |
| 7,422,852 B2 | 9/2008 | Gildea et al. |
| 7,598,390 B2 | 10/2009 | Bradford et al. |
| 7,619,059 B2 | 11/2009 | Kupcho et al. |
| 7,632,642 B2 | 12/2009 | Wangh et al. |
| 7,662,550 B1 | 2/2010 | Tyagi et al. |
| 7,776,529 B2 | 8/2010 | Dallwig et al. |
| 7,803,528 B1 | 9/2010 | Chiang et al. |
| 7,842,811 B2 | 11/2010 | Dallwig et al. |
| 7,847,076 B2 | 12/2010 | Mayrand |
| 7,892,741 B2 | 2/2011 | Gildea et al. |
| 7,968,289 B2 | 6/2011 | Coull et al. |
| 7,972,786 B2 | 7/2011 | Hartshorn et al. |
| 8,071,734 B2 | 12/2011 | Stanton et al. |
| 8,093,003 B2 | 1/2012 | Chiang et al. |
| 8,133,984 B2 | 3/2012 | Christensen |
| 8,211,644 B2 | 7/2012 | Hanna et al. |
| 8,247,171 B2 | 8/2012 | Nurmi et al. |
| 2003/0143606 A1 | 7/2003 | Olek et al. |
| 2004/0171046 A1 | 9/2004 | Berlin et al. |
| 2004/0181048 A1 | 9/2004 | Wang |

(Continued)

FOREIGN PATENT DOCUMENTS

WO 2012097903 A1 7/2012
WO 2012/178007 A1 12/2012

OTHER PUBLICATIONS

Kuroda A, Rauch TA, Todorov I, Ku HT, Al-Abdullah IH, Kandeel F, Mullen Y, Pfeifer GP, Ferreri K. Insulin gene expression is regulated by DNA methylation. PLoS One. Sep. 9, 2009; 4(9):e6953.*
Rakyan VK, Beyan H, Down TA, Hawa MI, Maslau S, Aden D, Daunay A, Busato F, Mein CA, Manfras B, Dias KR, Bell CG, Tost J, Boehm BO, Beck S, Leslie RD. Identification of type 1 diabetes-associated DNA methylation variable positions that precede disease diagnosis. PLoS Genet. Sep. 2011; 7(9):e1002300. Epub Sep. 29, 2011.*
Banerjee et al. A simple two-step protocol for the purification of human pancreatic beta cells. Diabetologia Apr. 1, 2009. vol. 52(4): 621-625.*
Genbank Accession No. J00265.1—Human insulin gene, complete cds (GI: 186429, first submitted on Apr. 27, 1993 and updated Jan. 7, 2010, retrieved on Mar. 8, 2014 from http://www.ncbi.nlm.nih.gov/nuccore/J00265).*

(Continued)

*Primary Examiner* — Angela M Bertagna
*Assistant Examiner* — Olayinka Oyeyemi
(74) *Attorney, Agent, or Firm* — Steven M. Hoffberg, Esq.; Ostrolenk Faber LLP

(57) ABSTRACT

A method for measuring blood levels of β cell DNA that is released upon β cell death by using a quantitative probe technology to detect amplified methylated and demethylated forms of the insulin gene DNA, representing normal tissue and β cell specific origin, respectively. Using probes permits the sensitive and specific identification of demethylated insulin DNA patterns that are present only in β cells. The method offers a bioassay for detecting β cell loss in diabetes, useful for screening of prediabetes, monitoring of disease progression, and selection and monitoring of therapies. The technique finds potential use in both Type I and Type II diabetes, as well as gestational diabetes.

23 Claims, 5 Drawing Sheets

(56) References Cited

U.S. PATENT DOCUMENTS

| | | | |
|---|---|---|---|
| 2006/0134663 A1 | 6/2006 | Harkin et al. | |
| 2007/0015156 A1 | 1/2007 | Goggins et al. | |
| 2007/0043216 A1 | 2/2007 | Bair et al. | |
| 2007/0141582 A1* | 6/2007 | Li et al. | 435/6 |
| 2007/0231797 A1 | 10/2007 | Fan et al. | |
| 2008/0034453 A1 | 2/2008 | Cheikh et al. | |
| 2010/0068720 A1* | 3/2010 | Li et al. | 435/6 |
| 2011/0104663 A1* | 5/2011 | Tetzner | 435/6 |

OTHER PUBLICATIONS

Bibikova et al. (2011a). High density DNA methylation array with single CpG site resolution. Genomics. Oct. 2011; 98(4):288-95. Epub Aug. 2, 2011.*

Bibikova et al. (2009b). Genome-wide DNA methylation profiling using Infinium® assay. Epigenomics. Oct. 2009; 1(1):177-200.*

Lichtenstein AV, Melkonyan HS, Tomei LD, Umansky SR. Circulating nucleic acids and apoptosis. Ann N Y Acad Sci. Sep. 2001; 945:239-49. Review.*

Campan M, Weisenberger DJ, Trinh B, Laird PW. MethyLight. Methods Mol Biol. 2009; 507:325-37.*

Dugast-Darzacq C, Grange T. MethylQuant: a real-time PCR-based method to quantify DNA methylation at single specific cytosines. Methods Mol Biol. 2009; 507:281-303.*

Volkmar et al. DNA methylation profiling identifies epigenetic dysregulation in pancreatic islets from type 2 diabetic patients. EMBO J. Mar. 21, 2012; 31(6):1405-26. Epub Jan. 31, 2012.*

Swarup V, Rajeswari MR. Circulating (cell-free) nucleic acids—a promising, non-invasive tool for early detection of several human diseases. FEBS Lett. Mar. 6, 2007;581(5):795-9. Epub Feb. 2, 2007. Review.*

Tyagi S, Kramer FR. Molecular beacons: probes that fluoresce upon hybridization. Nat Biotechnol. Mar. 1996; 14(3):303-8.*

Akirav Em, Lebastchi J, Galvan EM, Henegariu O, Akirav M, Ablamunits V, Lizardi PM, Herold KC. Detection of β cell death in diabetes using differentially methylated circulating DNA. Proc Natl Acad Sci U S A. Nov. 22, 2011; 108(47):19018-23. Epub Nov. 9, 2011.*

Rani, S., M. Clynes & L. O'Driscoll. 2007. Detection of amplifiable mRNA extracellular to insulin producing cells: potential for predicting beta cell mass and function. Clin. Chem. 53: 1936-1944.*

Christensen UB. EasyBeacons for the detection of methylation status of single CpG duplets. Methods Mol Biol. 2008; 429:137-60.*

Husseiny MI, Kuroda A, Kaye AN, Nair I, Kandeel F, Ferreri K. Development of a quantitative methylation-specific polymerase chain reaction method for monitoring beta cell death in type 1 diabetes. PLoS One. 2012; 7(10):e47942. Epub Oct. 29, 2012.*

Li LC, Dahiya R. MethPrimer: designing primers for methylation PCRs. Bioinformatics. Nov. 2002; 18(11):1427-31.*

Marras SA. Interactive fluorophore and quencher pairs for labeling fluorescent nucleic acid hybridization probes. Mol Biotechnol. Mar. 2008; 38(3):247-55. Epub Nov. 6, 2007.*

Akirav E, Kushner JA, Herold KC (2008) β-cell mass and type 1 diabetes: Going, going, gone? Diabetes 57:2883-2888.

Bluestone JA, Herold K, Eisenbarth G (2010) Genetics, pathogenesis and clinical interventions in type 1 diabetes. Nature 464:1293-1300.

Waldron-Lynch F, Herold KC (2009) Advances in type 1 diabetes therapeutics: Immunomodulation and β-cell salvage. Endocrinol Metab Clin North Am 38:303-317.

Bougneres PF, et al. (1988) Factors associated with early remission of type I diabetes in children treated with cyclosporine. N Engl J Med 318:663-670.

Keymeulen B, et al. (2005) Insulin needs after CD3-antibody therapy in new-onset type 1 diabetes. N Engl J Med 352:2598-2608.

Akirav, Eitan M. (2011) Detection of Beta Cell Death in Diabetes Using Differentially Methylated Circulating DNA, PNAAS Early Edition and Supplemental.

Snorgaard O, Lassen LH, Binder C (1992) Homogeneity in pattern of decline of β-cell function in IDDM: Prospective study of 204 consecutive cases followed for 7.4 yr. Diabetes Care 15:1009-1013.

Greenbaum CJ, et al.; Type 1 Diabetes Trial Net Research Group; European C-Peptide Trial Study Group (2008) Mixed-meal tolerance test versus glucagon stimulation test for the assessment of β-cell function in therapeutic trials in type 1 diabetes. Diabetes Care 31:1966-1971.

Steele C, et al. (2004) Insulin secretion in type 1 diabetes. Diabetes 53:426-433.

Erlich H, et al.; Type 1 Diabetes Genetics Consortium (2008) HLA DR-DQ haplotypes and genotypes and type 1 diabetes risk: Analysis of the Type 1 Diabetes Genetics Consortium families. Diabetes 57:1084-1092.

Hagopian WA, et al. (1995) Glutamate decarboxylase, insulin, and islet cell antibodies and HLA typing to detect diabetes in a general population-based study of Swedish children. J Clin Invest 95:1505-1511.

Verge CF, et al. (1996) Prediction of type I diabetes in first-degree rel. Diabetes 45: 926-933.

Sosenko JM, et al.; Diabetes Prevention Trial Type 1 Study Group (2007) Increasing the accuracy of oral glucose tolerance testing and extending its application to individuals with normal glucose tolerance for the prediction of type 1 diabetes: The Diabetes Prevention Trial Type 1. Diabetes Care 30:38-42.

Medarova Z, Tsai S, Evgenov N, Santamaria P, Moore A (2008) In vivo imaging of a diabetogenic CD8+ T cell response during type 1 diabetes progression. Magn Reson Med 59:712-720.

Klose RJ, Bird AP (2006) Genomic DNA methylation: The mark and its mediators. Trends Biochem Sci 31:89-97.

Bartke T, et al. (2010) Nucleosome-interacting proteins regulated by DNA and histone methylation. Cell 143:470-484.

Wang GG, Allis CD, Chi P (2007) Chromatin remodeling and cancer, part II: ATP-dependent chromatin remodeling. Trends Mol Med 13:373-380.

Miranda TB, Jones PA (2007) DNA methylation: The nuts and bolts of repression. J Cell Physiol 213:384-390.

Grady WM, Rajput A, Lutterbaugh JD, Markowitz SD (2001) Detection of aberrantly methylated hMLH1 promoter DNA in the serum of patients with microsatellite un- stable colon cancer. Cancer Res 61:900-902.

Wallner M, et al. (2006) Methylation of serum DNA is an independent prognostic marker in colorectal cancer. Clin Cancer Res 12:7347-7352.

Müller HM, et al. (2003) DNA methylation in serum of breast cancer patients: An independent prognostic marker. Cancer Res 63:7641-7645.

Poitout V, et al. (1995) Morphological and functional characterization of β TC-6 cells: An insulin-secreting cell line derived from transgenic mice. Diabetes 44:306-313.

Sherry NA, et al. (2006) Effects of autoimmunity and immune therapy on β-cell turnover in type 1 diabetes. Diabetes 55:3238-3245.

Jayaraman S (2011) Assessment of beta cell viability. Curr Protoc Cytom 55:6.27.1-6.27.16.

Kuroda A, et al. (2009) Insulin gene expression is regulated by DNA methylation. PLoS One 4:e6953.

Leiter EH, et al. (2007) Unexpected functional consequences of xenogeneic transgene expression in β3-cells of NOD mice. Diabetes Obes Metab 9(Suppl 2):14-22.

Trudeau JD, et al. (2000) Neonatal β-cell apoptosis: A trigger for autoimmune diabetes? Diabetes 49:1-7.

Fujimoto K, et al. (2010) Loss of Nix in Pdx1-deficient mice prevents apoptotic and necrotic β cell death and diabetes. J Clin Invest 120:4031-4039.

Berney T, et al. (2006) Detection of insulin mRNA in the peripheral blood after human islet transplantation predicts deterioration of metabolic control. Am J Transplant 6:1704-1711.

Best CH, Haist RE, Ridout JH (1939) Diet and the insulin content of pancreas. J Physiol 97:107-119.

Collins TJ (2007) ImageJ for microscopy. Biotechniques 43(Suppl 1):25-30.

Yang, B.T. (2011) Insulin Promoter DNA Methylation Correlates Negatively with Insulin Gene Expression and Positively with HbA1C Levels in Human Pancreatic Islets, Diabetologia 54:360-367.

(56) References Cited

OTHER PUBLICATIONS

Husseiny, Mohamed I. (2012) Development of a Quantitative Methylation-Specific Polymerase Chain Reaction Method for Monitoring Beta Cell Death in Type 1 Diabetes, PLOS ONE, vol. 7, Issue 10.

Darst, Russell P. (2010) Bisulfite Sequencing of DNA, Curr Protoc Mol Biol.; Chapter: Unit 7.917.

Ley, Timothy J. (1984) DNA Methylation and Regulation of the Human Beta-Globin-Like Genes in Mouse Erythroleukemia Cells Containing Human Chromosome 11, Proc. Natl. Acad. Sci. USA, vol. 81, pp. 6618-6622.

Akirav et al, Detection of Beta Cell Death in Diabetes Using Differentially Methylated Circulating DNA, Proc Nat Acad Sci, Nov. 22, 2011, vol. 108, No. 47, pp. 19018-19023.

Bibikova et al, Genome-Wide DNA Methylation Profiling Using Infinium Assay, Epigenomics, Oct. 2009, vol. 1, No. 1, pp. 177-200.

Kutyavin et al, 3'-Minor Groove Binder-DNA Probes Increase Sequence Specificity at PCR Extension Temperatures, Nucl Acids Res, Jan. 15, 2000, vol. 28, No. 2, pp. 655-661.

Tyagi et al, Molecular Beacons: Probes that Fluoresce Upon Hybridization, Nature Biotechnol, Mar. 1996, vol. 14, No. 3, pp. 303-308.

GenBank: ES210567.1.290382_2994_3970 *Arabidopsis* Ovule High Throughput cDNA Library *Arabidopsis thaliana* cDNA, mRNA sequence, Dec. 30, 2007, online, retrieved on Apr. 16, 2013 from inernet: <URL:http://www.ncbi.nlm.nih.gov/nucest/ES210567>.

GenBank: GO976425.1. CCIG1779.b1 CCIG Mimulus Guttatus DUN10 Fluoral Buds (H) Mimulus guttatus cDNA clone CCIG1779 5-, mRNA sequence, May 26, 2009, online, retrieved on Apr. 16, 2013 from interet: <URL:http://www.ncbi.nlm.nih.gov/nucest/GO976425>.

Johansson, Choosing Reporter-Quencher Pairs for Efficient Quenching Through Formation of Intramolecular Dimers 2 IN: Fluorescent Energy Transfer Nucleic Acid Probes: Designs and Protocols. 2006 Chapter 2, pp. 11-29.

Husseiny et al, Development of a Quantitative Methylation-specific Polymerase Chain Reaction Method for Monitoring Beta Cell Death in Type 1 Diabetes, PloS One, Oct. 29, 2012, vol. 7, No. 10, pp. 1-11.

Search Report, PCT/US13/28862, dated Jun. 10, 2013.

U.S. Appl. No. 13/784,017, document date: Dec. 19, 2013.

Sosenko et al., A Risk Score for Type 1 Diabetes Derived From Autoantibody-Positive Participants in the Diabetes Prevention Trial-Type 1, Diabetes Care, 30:38-42, Mar. 2008.

Dhawan et al., Pancreatic Beta Cell Identity is Maintained by DNA Methylation-Mediated Repression of Arx, Developmental Cell, 20:419-429, Apr. 19, 2011.

Levenson, DNA Methylation as a Universal Biomarker, Expert Rev Mol Diagn., 10(4):481-488, May 2010.

Volkmar et al, DNA Methylation Profiling Identifies Epigenetic Dysregulation in Pancreatic Islets from Type 2 Diabetic Patients, The EMBO Journal, 31:1405-1426, 2012.

\* cited by examiner

METHOD FOR USING PROBE BASED PCR DETECTION TO MEASURE THE LEVELS OF CIRCULATING DEMETHYLATED β CELL DERIVED DNA AS A MEASURE OF β CELL LOSS IN DIABETES

CROSS-REFERENCE TO RELATED APPLICATION

The present application claims priority to U.S. Provisional patent Application No. 61/606,140, filed Mar. 2, 2012, entitled METHOD FOR USING PROBE BASED PCR DETECTION TO MEASURE THE LEVELS OF CIRCULATING DEMETHYLATED β CELL DERIVED DNA AS A MEASURE OF β CELL LOSS IN DIABETES, the entire content of which is incorporated by reference herein.

BACKGROUND OF THE INVENTION

1. Field

The present application relates to compositions and methods for assessing β cell loss by quantitating extrapancreatic demethylated β cell derived DNA with methylation status-specific oligonucleotide probes that target Polymerase Chain Reaction (PCR)-amplified DNA sequences of genes that are uniquely expressed by β cells.

The loss of insulin producing β cells results in glucose intolerance and the development of Type 1(T1D) and Type 2 (T2D) diabetes. Eitan Akirav, Jake A. Kushner and Kevan C. Herold, "β-Cell Mass and Type 1 Diabetes Going, Going, Gone?", doi: 10.2337/db07-1817 Diabetes November 2008 vol. 57 no. 11 2883-2888. Currently, evaluation of β cell mass is carried out by measuring β cell products such as c-peptide. While useful, these measures do not provide real time information about active β cell loss.

There has thus been a long-felt need for a method capable of accurately evaluating β cell death so as to improve disease diagnosis, allow for disease staging, and provide a better evaluation of clinical treatment efficacy. There is further a great need in the art for compositions and methods for non-invasively monitoring β cell destruction in individuals having, or at risk of developing, diabetes mellitus ("diabetes"), including Type-1 and Type-2 Diabetes (T1D and T2D, respectively), as well as gestational diabetes.

Epigenetic modifications of DNA control cell-type specific gene expression. DNA methylation is one example of an epigenetic modification that affects gene. Methylation of DNA occurs at CpG dinucleotide sites, and this modification maintains a transcriptionally repressive chromatin configuration (Miranda et al., 2007, J. Cell Physiol. 213:384-390). Conversely, demethylation of CpG dinucleotide sites allows a transcriptionally permissive configuration (Id). Beta cells express insulin, and thus, maintain a transcriptionally-permissive hypomethylated regulatory region for the insulin gene (INS). Indeed, Genomic DNA sequences near the insulin gene are methylated in non-β cell cell types. Ley, Timothy J., et al. "DNA methylation and regulation of the human beta-globin-like genes in mouse erythroleukemia cells containing human chromosome 11." Proceedings of the National Academy of Sciences 81.21 (1984): 6618-6622.) Therefore, the presence of hypomethylated insulin gene DNA outside of the pancreas of a subject correlated with the release of hypomethylated insulin gene DNA from dead and dying (e.g., apoptotic) β cells. Id. and Kuroda A, Rauch T A, Todorov I, Ku H T, Al-Abdullah I H, et al. (2009) Insulin Gene Expression Is Regulated by DNA Methylation. PLoS ONE 4(9): e6953. doi:10.1371/journal.pone.0006953.

SUMMARY OF THE INVENTION

A method is provided for the detection of extrapancreatic circulating β cell-derived DNA that is indicative of acute and chronic β cell destruction, and thus provides an early biomarker for β cell death in human tissues, serum and other bodily fluids, such as saliva. The method can identify β cell death before the onset of hyperglycemia and diabetes. This strategy may prove useful for monitoring β cell destruction in individuals at risk for the development of diabetes, monitoring the progression of β cell destruction in individuals with diabetes, and use as a marker to guide therapy in patients with diabetes with possible ongoing β cell destruction.

In various embodiments, methods of the invention assesses the presence of β cell-derived DNA that is released upon β cell death by using a quantitative probe technology in a traditional PCR assay. By using probes, the method permits one to identify demethylated insulin DNA patterns that are present only in β cells. Therefore, the method provides a bioassay for detecting β cell loss in diabetes to provide a method capable of improving disease diagnosis, allowing for disease staging, and providing a better evaluation of clinical treatment efficacy. In various embodiments of the invention detects β cell loss associated with T1D, T2D, or gestational diabetes, or any combination thereof.

The method as disclosed herein uses a stepwise detection and analysis of β cell and non-β cell derived insulin DNA. The key principle behind the method is the existence of unique DNA methylation patterns in the β cells that are absent from other cells in the body. That is, the islet β cell DNA methylation pattern associated with the insulin gene is reasonably unique, and the level of islet β cell-origin insulin gene DNA in the serum and other body fluids is altered by islet β cell death or pathology.

By first conducting a bisulfate conversion of DNA extracted from a bodily fluid of an individual, it becomes possible to quantify the relative abundance of β cell insulin DNA in the circulation, and hence whether that individual is experiencing β cell loss.

A method is developed for detecting B cell death in vivo by amplifying regions of genes that: i) are expressed in β cells (e.g., INS); and ii) contain CpG methylation sites, and then measuring the proportion of β cell-derived DNA in the serum or other body fluids. Generally, by using probes that are specific for DNA methylation patterns in β cells, circulating copies of β cell-derived demethylated DNA are detected after bisulfite treatment and PCR amplification. See, Darst R P, Pardo C E, Ai L, Brown K D, Kladde M P; "Bisulfite sequencing of DNA", Curr Protoc Mol Biol. 2010 July; Chapter 7: Unit 7.9.1-17. doi: 10.1002/0471142727.mb0709s91; "Methylation Analysis by Bisulfite Sequencing: Chemistry, Products and Protocols from Applied Biosystems", tools.invitrogen.com/content/sfs/manuals/cms_039258.pdf, each of which is expressly incorporated herein by reference. The method provides a noninvasive approach for detecting β cell death in vivo that may be used to track the progression of diabetes and guide its treatment.

It is likewise understood that specific other tissues and cell types may have distinct methylation patterns from other tissues, and therefore that a corresponding technique, using appropriate PCR primers and detection probes, may be used to detect apoptosis or other DNA release from these specific tissues or cell types into body fluids.

As an alternate to serum, saliva may also contain sufficient DNA containing epigenetic DNA modifications to provide a basis for diagnosis. During cell death most of the nuclear DNA is converted into nucleosomes and oligomers (Umansky, S. R., et al. [1982], "In vivo DNA degradation of thymocytes of gamma-irradiated or hydrocortisone-treated rats"; Biochim. Biophys. Acta 655:9-17), which are finally digested by macrophages or neighboring cells. However, a portion of this degraded DNA escapes phagocytic metabolism, and can be found in the bloodstream (Lichtenstein, A. V., et al. [2001], "Circulating nucleic acids and apoptosis"; Ann NY Acad Sci, 945:239-249), and also in bodily fluids. The present invention addresses the detection of beta cell-specific epigenetic modifications that are detectable in bodily fluids such as plasma and saliva following the destruction of beta cells.

A method is provided for the sensitive and specific detection of β cell death in vivo in models of autoimmune and chemically induced diabetes in mice, in human tissues, and in serum from patients with T1D and T2D. This assay identifies a specific methylation pattern in the β cell insulin DNA. This method provides a biomarker for detecting β cell loss in prediabetic mammals during progression of diabetes.

A preferred method thus comprises the following steps:

1) Serum/plasma, or other body fluid is collected and DNA is extracted and substantially purified. Serum is reasonably available and usable, but collection of saliva may be deemed less invasive.

2) Purified DNA is treated with bisulfite, whereupon the bisulfite converts demethylated cytosines to uracil while sparing the methylated cytosines (see "Methylation Analysis by Bisulfite Sequencing: Chemistry, Products and Protocols from Applied Biosystems", Invitrogen Corp. (2007) tools.invitrogen.com/content/sfs/manuals/cms_039258.pdf, expressly incorporated herein by reference in its entirety) (other methylation-sensitive distinctions may be exploited to distinguished between methylated and demethylated DNA, as known in the art).

3) Circulating DNA exists in relatively low abundance. Therefore, bisulfite treated DNA is subject to a $1^{st}$ step PCR. This reaction is methylation insensitive and is designed to increase the availability of DNA template. PCR products are run on a standard gel electrophoresis and purified. Since the DNA is previously bisulfate treated, there will be distinct DNA subpopulations corresponding to methylated and demethylated insulin gene DNA.

4) Purified DNA is used for a methylation sensitive reaction, that is, the reaction distinguishes between amplified DNA corresponding to methylated insulin gene DNA and demethylated insulin gene DNA (i.e., from β cells). The reaction uses methylation sensitive probes to detect and differentiate demethylated insulin DNA from β cell origin from methylated insulin DNA of non-β cell origin.

Optionally, relative numbers of β cell derived DNA are presented as "methylation index" or $2^{(methylated\ DNA-demethylated\ DNA)}$ or the difference between methylated DNA and demethylated DNA. Other quantitative analysis of the results, as well as historical trend analysis is possible. Further, the amount of β cell derived DNA may be normalized on a different basis than non-β cell derived DNA representing the insulin gene. For example, a tracer similar in characteristics to the β cell derived DNA (but unique with respect to endogenous DNA) may be quantitatively injected into a patient.

5) Provide a quantitative reference for the amount of β cell derived DNA normalized for dilution, degradation, secretion/excretion factors, etc.

It is therefore an object to provide a method for monitoring beta cell death, comprising: extracting and purifying DNA from a body fluid of an animal; treating the extracted purified DNA with bisulfite to convert demethylated cytosine to uracil while sparing the methylated cytosines; amplifying the bisulfite-treated DNA using polymerase chain reaction; purifying the amplified bisulfite-treated DNA; performing a methylation sensitive reaction on the purified bisulfite-treated DNA using at least two different methylation specific probes which quantitatively distinguish between demethylated insulin DNA of β cell origin and methylated insulin DNA of non-β cell origin; and computing a quantitative relationship between methylated insulin DNA and demethylated insulin DNA.

It is a further object to provide a method for monitoring cell death of a cell type having at least one DNA portion that has a unique DNA CpG methylation pattern as compared to other cells, which is released into body fluids upon cell death of cells of the cell type, comprising: extracting and purifying DNA that comprises the DNA portion; treating the extracted purified DNA with bisulfite to convert cytosine to uracil while sparing the CpG methylated cytosines; amplifying a region of the bisulfite-treated DNA that comprises the DNA portion by polymerase chain reaction using DNA CpG methylation pattern independent primers; determining a quantitative relationship between the DNA portion having the unique DNA CpG methylation pattern to the DNA portion lacking the unique DNA CpG methylation pattern, by employing the DNA CpG methylation pattern-specific probes; computing a difference between the DNA portion having the unique DNA CpG methylation pattern and the DNA portion lacking the unique DNA CpG methylation pattern.

Another object provides a method for monitoring beta cell death, comprising: extracting and purifying genomic DNA from a body fluid of an animal, wherein the genomic DNA comprises at least a portion of a gene that is predominantly expressed by β cells and that contains a CpG methylation site; treating the genomic DNA with bisulfite; performing a polymerase chain reaction (PCR) with primers that flank a region of the genomic DNA that comprises the CpG methylation site; purifying the PCR products; melting the PCR products into single strands; hybridizing the single-stranded PCR products with a first oligonucleotide probe capable of hybridizing with a target sequence that comprises a site corresponding to a bisulfite-converted CpG site and a second oligonucleotide probe capable of hybridizing with a target sequence that comprises a site corresponding to a bisulfite-nonconverted CpG site, and wherein the probes each comprise a non-FRET label pair consisting of a fluorophore and a quencher, and wherein interaction of the first oligonucleotide probe or second oligonucleotide probe with a respective target causes the first oligonucleotide probe or second oligonucleotide probe to change from a first conformation to a second conformation, thereby changing the distance between the fluorophore and quencher of said label pair, and wherein in only one conformation do the fluorophore and quencher interact sufficiently to quench the fluorescence of the fluorophore by a predetermined amount; quantitatively measuring fluorescent signals emitted by the first oligonucleotide probe and the second oligonucleotide probe; and reporting a quantitative relationship of the fluorescent signal emitted by the first oligonucleotide probe and the second oligonucleotide probe, indicative of the relative amount of β cell-derived DNA versus non-β cell-derived DNA.

It is also an object to provide a kit for detecting β cell-derived demethylated genomic DNA in a biological sample, wherein the kit comprises: PCR primers that flank a portion of a gene that is predominantly expressed by β cells and contains a CpG methylation site; a first oligonucleotide probe capable of hybridizing with a first target sequence on a PCR product made using the PCR primers, wherein the first target sequence corresponds to at least one bisulfite-converted CpG site of the portion of the gene; and a second oligonucleotide probe capable of hybridizing with a target sequence on a PCR product made using the PCR primers of the kit, wherein the target sequence corresponds to at least one bisulfite-nonconverted CpG site of the portion of the gene, wherein the first oligonucleotide probe and the first oligonucleotide probe each comprise label that allows selective quantitation of the first oligonucleotide probe and the second oligonucleotide probe. Each probe may comprise a label pair consisting of a fluorophore and a quencher, and wherein a binding interaction of the first oligonucleotide probe with the first target sequence, and the second oligonucleotide probe with the second target sequence, causes a change from a first conformation to a second conformation, thereby changing an interaction between the fluorophore and quencher of said label pair, and wherein in only one conformation of the first and second conformations do the labels interact sufficiently to quench the fluorescence of the fluorophore by at least 25 percent.

The probes may be conjugated to a fluorophore and/or a quencher. The fluorophore may be at least one of 6-carboxy fluorescein and tetrachlorofluorescein. The quencher may be tetramethylrhodamine. The probe may employ a fluorescent resonant energy transfer (FRET) interaction between the fluorophore and quencher, wherein the fluorophore and quencher are selectively separated in dependence on a binding of the probe to a respective target. The probe may also employ a non-FRET interaction between the fluorophore and quencher, wherein the fluorophore and quencher have an interaction based on a conformation of the probe, and in which the conformation is selectively dependent on a binding of the probe to a respective target.

The methylation sensitive reaction may comprises quantitatively determining a release of a fluorophore from a probe bound to the purified bisulfite-treated DNA.

The DNA portion having the unique DNA CpG methylation pattern may comprise an insulin gene from a pancreatic beta cell. The body fluid may be, for example, blood, blood plasma, blood serum, saliva, or tears.

DETAILED DESCRIPTION

Figure 1:
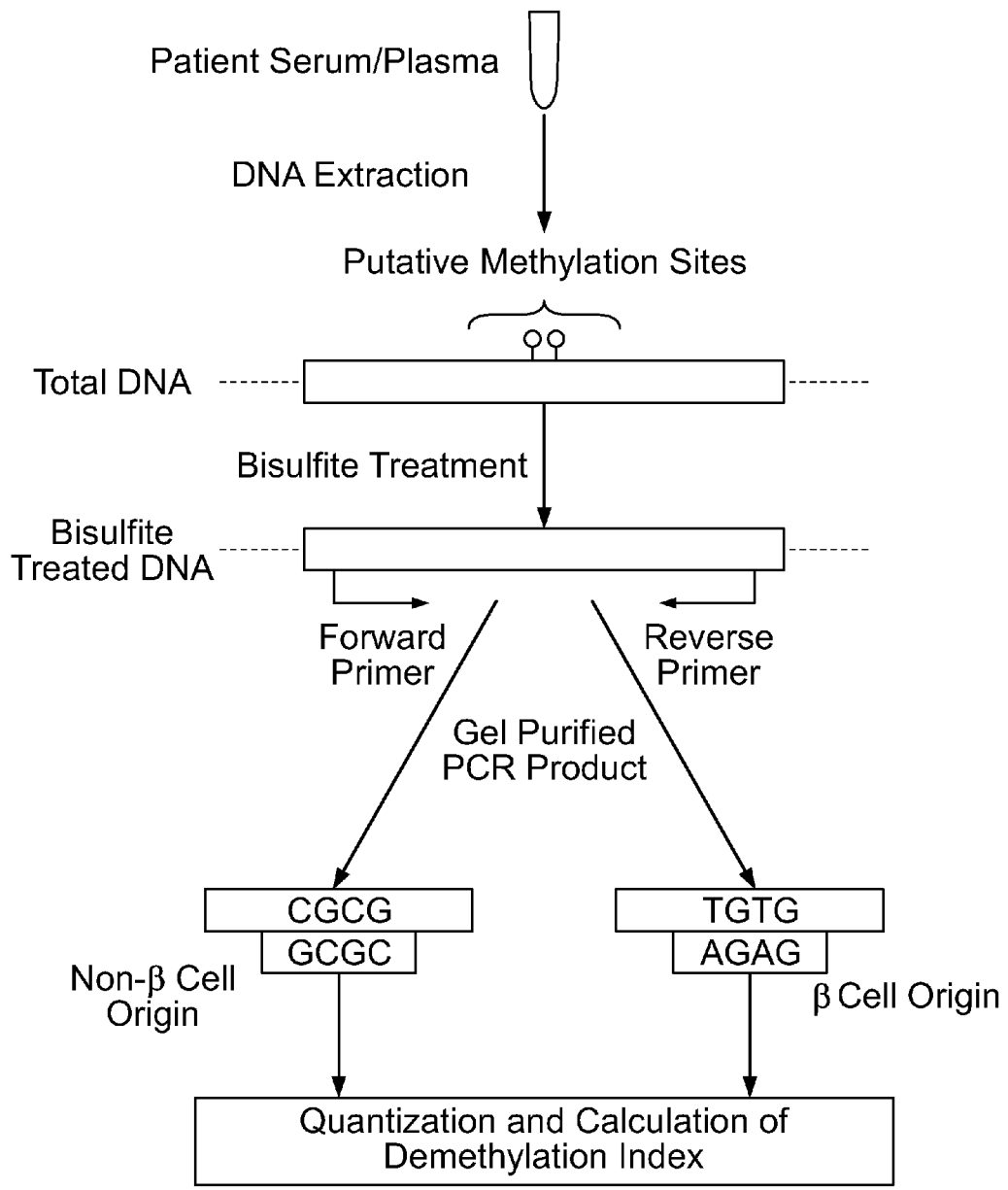
FIG. 1 sets forth the overall procedure for detecting circulating β cell DNA.

In various embodiments, the present technology substantially isolates nucleic acids from a sample of body fluid, for example blood plasma, saliva, spinal fluid, lymph fluid, synovial fluid, or tears, for example.

Various DNA extraction, isolation and purification technologies can be used, for example as taught in U.S. Pat. Nos. 4,935,342, 5,990,301, 6,020,124, 7,241,596, 6,485,903, 6,214,979, Re. 39,920 each of which is expressly incorporated herein by reference in its entirety.

An anion exchange material may be selected and employed which effectively adsorbs the target nucleic acids or protein complexes thereof. For example, commercially available anion exchange materials may be employed. Either strong or weak anion exchangers may be employed. A preferred weak exchanger can be one in which primary, secondary, or tertiary amine groups (i.e., protonatable amines) provide the exchange sites. The strong base anion exchanger has quaternary ammonium groups (i.e., not protonatable and always positively charged) as the exchange sites. Both exchangers can be selected in relation to their respective absorption and elution ionic strengths and/or pH for the nucleic acid being separated. Purification by anion exchange chromatography is described in U.S. Pat. No. 5,057,426 (see also EP 0 268 946 B1), expressly incorporated by reference herein in its entirety.

The material which is commercially available under the designation Q-Sepharose™ (GE Healthcare) is a particularly suitable. Q-Sepharose™, can be a strong anion exchanger based on a highly cross-linked, bead formed 6% agarose matrix, with a mean particle size of 90 μm. The Q-Sepharose™ can be stable in all commonly used aqueous buffers with the recommended pH of 2-12 and recommended working flow rate of 300-500 cm/h. In other preferred embodiments, the anion-exchange medium can be selected from sepharose-based quaternary ammonium anion exchange medium such as Q-filters or Q-resin.

The chromatographic support material for the anion charge used in the instant methods can be a modified porous inorganic material. As inorganic support materials, there may be used materials such as silica gel, diatomaceous earth, glass, aluminum oxides, titanium oxides, zirconium oxides, hydroxyapatite, and as organic support materials, such as dextran, agarose, acrylic amide, polystyrene resins, or copolymers of the monomeric building blocks of the polymers mentioned.

The nucleic acids can also be purified by anion exchange materials based on polystyrene/DVB, such as Poros 20 for medium pressure chromatography, Poros™ 50 HQ, of the firm of BioPerseptive, Cambridge, U.S.A., or over DEAE Sepharose™ DEAE Sephadex™ of the firm of Pharmacia, Sweden; DEAE Spherodex™, DEAE Spherosil™, of the firm of Biosepra, France.

A body fluid sample, such as blood plasma or saliva, containing nucleic acids or their proteinous complexes, is applied to the selected anion exchange material, and the nucleic acids or their complexes become adsorbed to the column material.

The contact and subsequent adsorption onto the resin can take place by simple mixing of the anion exchange media with the body fluid, with the optional addition of a solvent, buffer or other diluent, in a suitable sample container such as a glass or plastic tube, or vessel commonly used for handling biological specimens. This simple mixing referred to as batch processing, can be allowed to take place for a period of time sufficiently long enough to allow for binding of the nucleoprotein to the media, preferably 10 to 40 min. The media/complex can then be separated from the remainder of the sample/liquid by decanting, centrifugation, filtration or other mechanical means.

The anion exchange material can optionally be washed with an aqueous solution of a salt at which the nucleic acids remain bound to the anion exchange material, the washing being of sufficient volume and ionic strength to wash the non-binding or weakly binding components through the anion-exchange material. In some embodiments, the resin can be washed with 2×SSC (300 mM NaCl/30 mM sodium citrate (pH 7.0). Preferred ranges of the salt solutions are 300-600 nM NaCl/30 mM sodium citrate (pH 7.0). The resin may alternately be washed with 300-600 mM LiCl/10 mM NaOAc (pH 5.2).

The bound nucleic acids may then be eluted by passing an aqueous solution through the anion exchange material of increasing ionic strength to remove in succession proteins that are not bound or are weakly bound to the anion-exchange material and the nucleic acids of increasing molecular weight from the column. Both proteins and high and low molecular weight nucleic acids (as low as 10 base pairs) can be selectively eluted from the resin stepwise with the salt solution of concentrations from 300 mM to 2.0 M of NaCl and finally with 2.0 M guanidine isothiocyanate. LiCl solutions in the concentration range of 300 mM to 2.0 M of LiCl may also be used for stepwise elution.

The nucleic acids isolated may be in double-stranded or single-stranded form.

The body fluid can be pre-filtered through a membrane and supplemented with 10 mM EDTA (pH 8.0) and 10 mM Tris-HCL (pH 8.0) prior to adsorption onto the anion-exchange medium. Commercial sources for filtration devices include Pall-Filtron (Northborough, Mass.), Millipore (Bedford, Mass.), and Amicon (Danvers, Mass.). Filtration devices which may be used are, for example, a flat plate device, spiral wound cartridge, hollow fiber, tubular or single sheet device, open-channel device, etc.

The surface area of the filtration membrane used can depend on the amount of nucleic acid to be purified. The membrane may be of a low-binding material to minimize adsorptive losses and is preferably durable, cleanable, and chemically compatible with the buffers to be used. A number of suitable membranes are commercially available, including, e.g., cellulose acetate, polysulfone, polyethersulfone, and polyvinylidene difluoride. Preferably, the membrane material is polysulfone or polyethersulfone.

The body fluid, for example blood plasma or saliva, can be supplemented with EDTA and Tris-HCL buffer (pH 8.0) and digested with proteinases, such as for example Proteinase K, prior to adsorption onto the anion exchange medium.

The anion-exchange medium can be immobilized on an individualized carrier such as a column, cartridge or portable filtering system which can be used for transport or storage of the medium/nucleoprotein bound complex. The nucleic acid/anion exchange may be maintained in storage for up to 3 weeks.

A kit may be provided with a solid carrier capable of adsorbing the nucleic acids containing in a sample of a body fluid, for example blood plasma or saliva. The kit may also contain other components for example, reagents, in concentrated or final dilution form, chromatographic materials for the separation of the nucleic acids, aqueous solutions (buffers, optionally also in concentrated form for final adjusting by the user) or chromatographic materials for desalting nucleic acids which have been eluted with sodium chloride.

The kit may also contain additional materials for purifying nucleic acids, for example, inorganic and/or organic carriers and optionally solutions, excipients and/or accessories. Such agents are known and are commercially available. For solid phase nucleic acid isolation methods, many solid supports have been used including membrane filters, magnetic beads, metal oxides, and latex particles. Widely used solid supports include silica-based particles (see, e.g., U.S. Pub. Pat. App. 2007/0043216 (Bair Jr., et al.); U.S. Pat. No. 5,234,809 (Boom et al.); WO 95/01359 (Colpan et al.); U.S. Pat. No. 5,405,951 (Woodard); WO 95/02049 (Jones); WO 92/07863 (Qiagen GmbH), each of which is expressly incorporated herein by reference). Inorganic components of carriers may be, for example, porous or non-porous metal oxides or mixed metal oxides, e.g. aluminum oxide, titanium dioxide, iron oxide or zirconium dioxide, silica gels, materials based on glass, e.g. modified or unmodified glass particles or ground glass, quartz, zeolite or mixtures of one or more of the above-mentioned substances. On the other hand, the carrier may also contain organic ingredients which may be selected, for example, from latex particles optionally modified with functional groups, synthetic polymers such as polyethylene, polypropylene, polyvinylidene fluoride, particularly ultra high molecular polyethylene or HD-polyethylene, or mixtures of one or more of the above-mentioned substances.

In addition, the reagent kit may also contain excipients such as, for example, a protease such as proteinase K, or enzymes and other agents for manipulating nucleic acids, e.g. at least one amplification primer, and enzymes suitable for amplifying nucleic acids, e.g. DNase, a nucleic acid polymerase and/or at least one restriction endonuclease. Alternately, a commercial polymerase chain reaction kit may be used to amplify the DNA samples, as discussed below. DNA is subject to degradation by DNases present in bodily fluids, such as saliva. Thus, in certain embodiments, it is advantageous to inhibit DNase activity to prevent or reduce the degradation of DNA so that sufficiently large sequences are available for detection.

After collection, the sample may be treated using one or more methods of inhibiting DNase activity, such as use of ethylenediaminetetraacetic acid (EDTA), guanidine-HCl, GITC (Guanidine isothiocyanate), N-lauroylsarcosine, Na-dodecylsulphate (SDS), high salt concentration and heat inactivation of DNase.

After collection, the sample may be treated with an adsorbent that traps DNA, after which the adsorbent is removed from the sample, rinsed and treated to release the trapped DNA for detection and analysis. This not only isolates DNA from the sample, but, some adsorbents, such as Hybond™ N membranes (Amersham Pharmacia Biotech Ltd., Piscataway, N.J.) protect the DNA from degradation by DNase activity.

In some cases, the amount of DNA in a sample is limited. Therefore, for certain applications, sensitivity of detection may be increased by known methods.

Where DNA is present in minute amounts, larger samples can be collected and thereafter concentrated such as by butanol concentration or concentration using Sephadex™ G-25 (Pharmacia Biotech, Inc., Piscataway N.J.).

Once obtained, the bodily fluid derived DNA may be used as an alternate to serum-derived DNA as discussed below.

Since the technology is ratiometric, it is dependent not on the absolute quantity of DNA available, but the proportional relationships of the methylated and unmethylated portions. In general, the disposition of these types in the various body fluids is not believed to be highly dependent on the fluid type, and calibration techniques can be used to account for persistent and predictable differences in the fluid methylated/unmethylated ratios.

Bisulfite Treatment

DNA from serum samples was purified using the Qiagen QIAamp DNA Blood Kit following the manufacturer-recommended protocol. Synthetic unmethylated and methylated DNA was purchased from Zymo research. DNA was then subjected to bisulfite treatment and purified on a DNA binding column to remove excessive bisulfite reagent using the Zymo EZ DNA Methylation Kit.

First-Step PCR and Gel Extraction.

A methylation-independent reaction was carried out to increase the DNA template for PCR analysis.

For the reaction, bisulfite-treated DNA template was added to Zymo Taq Premix. The amplification proceeded for, e.g., 50 cycles. The PCR products were excised from a 3% agarose gel. Negative controls without DNA did not yield products in the first-step reaction.

PCR products obtained using methylation-independent primers were purified using a Qiagen PCR Purification Kit.

Methylation-Specific Analysis

Methylation-specific DNA probes are used for the detection of β cell derived DNA. These probes are able to quantitatively and sensitively detect circulation demethylated and methylated DNA from a β cell and a non-β cell origin, respectively. The new probes replace the previously published methylation specific primers (see Akirav E M, Lebastchi J, Galvan E M, Henegariu O, Akirav M, Ablamunits V, Lizardi P M, and Herold K C. Detection of β cell death in diabetes using differentially methylated circulating DNA. PNAS, 2011, Proceedings of the National Academy of Sciences, 2011, November:108(19018-23), expressly incorporated herein by reference, hereinafter Akirav et al. (2011). See also Husseiny M I, Kuroda A, Kaye A N, Nair I, Kandeel F, et al. (2012) Development of a Quantitative Methylation-Specific Polymerase Chain Reaction Method for Monitoring Beta Cell Death in Type 1 Diabetes. PLoS ONE 7(10): e47942. doi: 10.1371/journal.pone.0047942, expressly incorporated herein by reference), which presented with a relatively low specificity (i.e. demethylated primers detected methylated DNA and vice versa). Low specificity negatively impacts assay sensitivity by decrease detection limits of β cell derived demethylated DNA. Low DNA levels are presumably present during early β cell loss, such as prediabetes. See, U.S. Pat. No. 6,150,097, expressly incorporated herein by reference.

The overall procedure for the detection of circulating β cell DNA is depicted in FIG. 1. The steps leading to the use of probes are identical with those described in Akirav et al. (2011), which discloses the use of methylation-specific primers (and not probes) to detect β cell derived DNA. The primers were able to detect demethylated and methylated DNA from a β cell and a non-β cell origin, respectively. While useful, these primers had a relatively low specificity whereby demethylated primers detected methylated DNA and vice versa. Low specificity reduced assay sensitivity as it impaired the ability to detect very low levels of β cell-derived DNA, such as in the condition of early β cell loss and pre-diabetes.

DNA from serum samples was purified using the Qiagen QIAamp DNA Blood Kit following the manufacturer-recommended protocol. Synthetic unmethylated and methylated DNA was purchased from Millipore. Purified DNA was quantitated using a NanoDrop 2000 spectrophotometer. DNA was then subjected to bisulfite treatment and purified on a DNA binding column to remove excessive bisulfite reagent using the Zymo EZ DNA Methylation Kit.

The present method, in contrast, uses probe DNA that offers a significant improvement in sensitivity over the primers used in the prior art discussed above. That is, probe DNA allows for a highly specific recognition of two demethylated sites in the insulin gene. This tends to eliminate false positive readings and thus provides increased assay specificity and sensitivity. The following is used as probe for the detection of circulating DNA in the assay according to the present method:

A methylation-independent reaction was carried out to increase the DNA template for PCR analysis. For the reaction, bisulfite-treated DNA template was added to Zymo Taq™ Premix. The following PCR primers are used to amplify the human insulin position 2122220-2121985 on chromosome 11, GRCh37.p10, October 2012):

```
Forward primer:
                                  SEQ ID NO: 001
GTGCGGTTTATATTTGGTGGAAGTT Reverse primer:
                                  SEQ ID NO: 002
ACAACAATAAACAATTAACTCACCCTACAA
```

Using the forward and reverse primers, PCR was conducted The PCR products were excised from a 3% agarose gel.

The PCR product (or amplicon) is detect by methylation status specific probes as follows:

a) Probes for the detection of methylated insulin DNA (i.e., DNA not derived from a β cell) (alternates):

```
                                  SEQ ID NO: 003
         ACCTCCCGACGAATCT

SEQ ID NO: 004
         TACCTCTCGTCGAATCT
``` b) Probes for the detection of demethylated insulin DNA (i.e., DNA derived from a β cell)(alternates):

```
                                  SEQ ID NO: 005
         ACCTCCCAACAAATCT

SEQ ID NO: 006
         TACCTCCCATCAAATCT
```

In various embodiments, the methylation status-specific probes are conjugated with 6-carboxyfluorescein, abbreviated as F AM, thus permitting quantitative detection. Other technologies may be used in conjunction with the present method; see, U.S. Pat. Nos. 6,103,476, 8,247,171, 8,211,644, 8,133,984, 8,093,003, 8,071,734, 7,972,786, 7,968,289, 7,892,741, 7,847,076, 7,842,811 7,803,528, 7,776,529, 7,662,550, 7,632,642, 7,619,059, 7,598,390, 7,422,852, 7,413,708, 7,399,591, 7,271,265, 7,241,596, 7,183,052, 7,153,654, 7,081,336, 7,070,933, 7,015,317, 7,005,265, 6,811,973, 6,680,377, 6,649,349, 6,548,254, 6,485,903, 6,485,901, each of which is expressly incorporated in its entirety. Probes may be Flourescent Resonance Energy Transfer (FRET) or non-FRET type. See, U.S. Pat. No. 6,150, 097, expressly incorporated herein by reference.

c) PCR is done with an annealing temperature of 60° C. for 50 cycles and quantified using a Real Time PCR machine. A range of 52-65° C. for the PCR would be acceptable.

d) Values generated by demethylated probes are subtracted from values of methylated probes and a delta calculated.

Figure 2A:
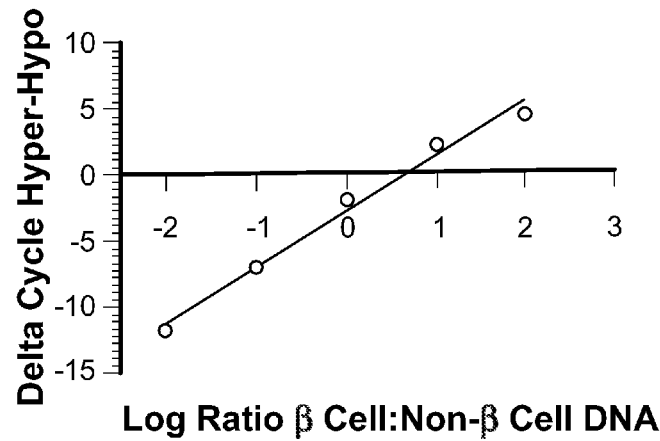
FIG. 2A shows the results of testing logarithmic serial dilutions of synthetic hypomethylated and hypermethylated DNA.
Figure 2B:
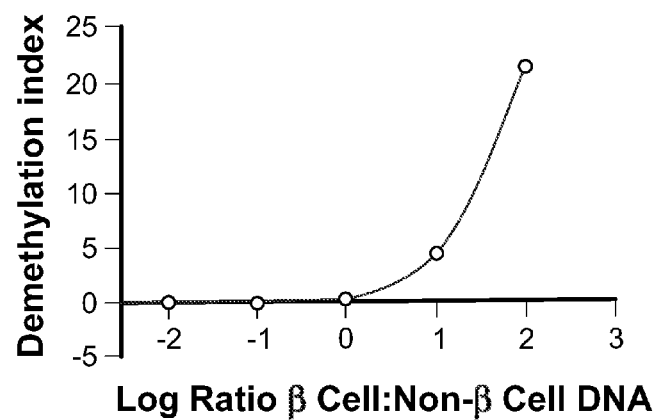
FIG. 2B shows that $Log_{10}$ transformation of demethylation index measurements show a non-linear fit.
Figure 2C:
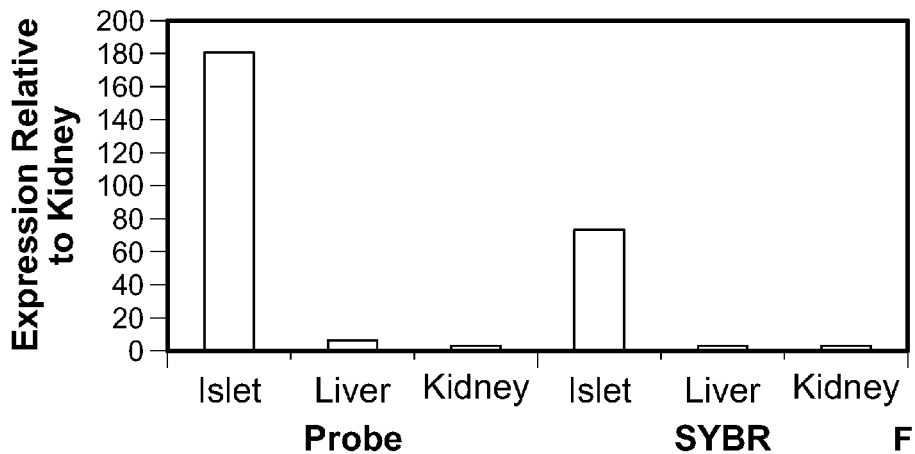
FIG. 2C shows the increase in specificity and sensitivity of the assay used in the present method.

Probe testing of logarithmic serial dilutions of synthetic hypomethylated and hypermethylated DNA has shown a linear behavior ($R^2$=0.98) of the delta between hypermethylated DNA and hypomethylated DNA (delta=hypermethylated DNA-hypomethylated DNA) over a wide range of DNA dilution (range is 4 log scale) see FIG. 2A. $Log_{10}$ transformation of demethylation index measures show a nonlinear fit ($r^2$=0.9999, DF 2) see FIG. 2B. FIG. 2C shows the specificity of the assay. The probe detects demethylated DNA at ~180 folds in islet (where β cells reside) compared with liver and kidney which do not express insulin. In contrast, primers detect the demethylated DNA at ~80 fold. In other words probes used according to an embodiment of the present invention are 2.25 times more specific than primers the primers used in accordance with Akirav et al. (2011). Akirav (2011) analyzed the linearity of the ratio between the two DNA species by mixing demethylated DNA (derived from β cells) and methylated DNA (derived from non-β cells) and measuring the difference in cycle threshold (Ct) values detected. The difference in the Ct values of the methylated and demethylated products of the second-step PCR corresponds to quantitative differences in the quantity of DNA. There was a linear relationship between the log ratio of β-cell-derived and non-β-cell-derived DNA and a demethylation index between 100:1 and 1:100 ($r^2$=0.957; P<0.01). Therefore, the present technology has superior linearity.

Figure 3A:
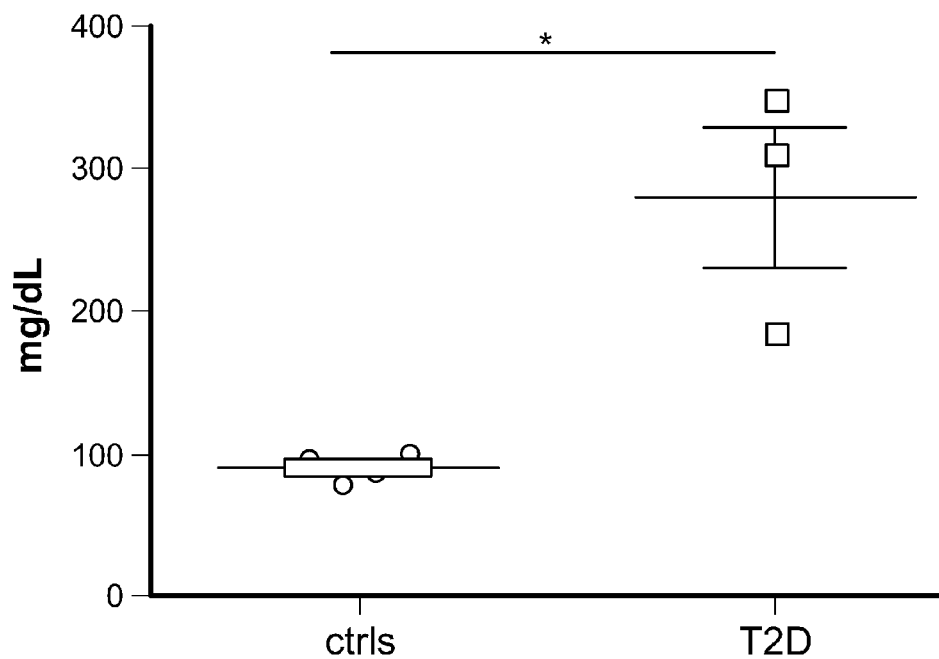
FIG. 3A demonstrates improved glucose levels in patients with long-standing Type 2 diabetes.
Figure 3B:
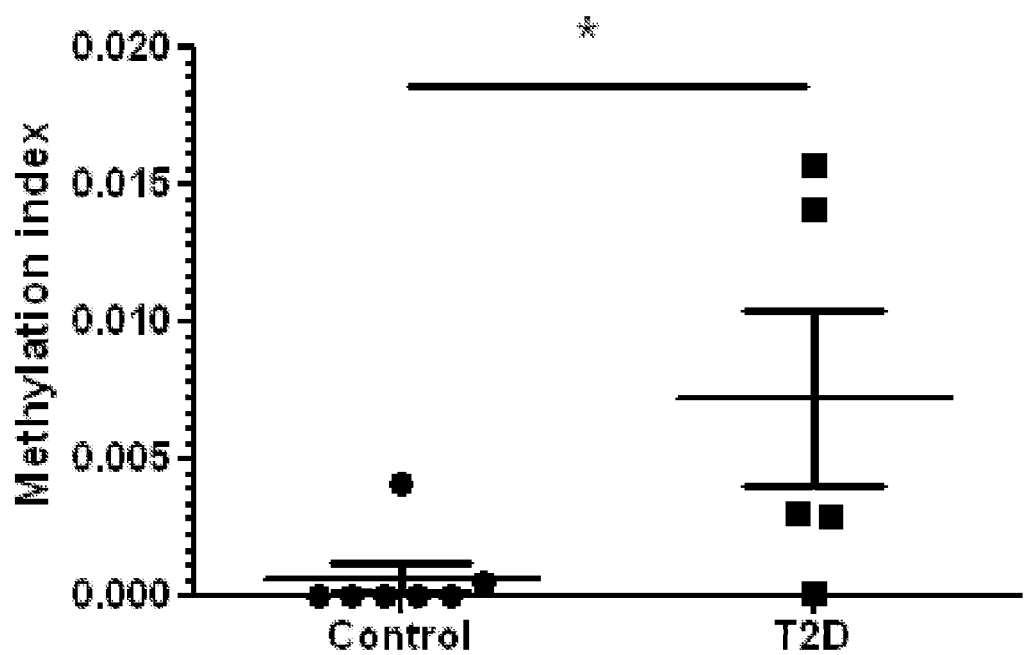
FIG. 3B shows that the probes according to the present technology reveal a significant increase in demethylated β cell DNA in the serum of the patients with long-standing Type 2 diabetes.
Figure 3C:
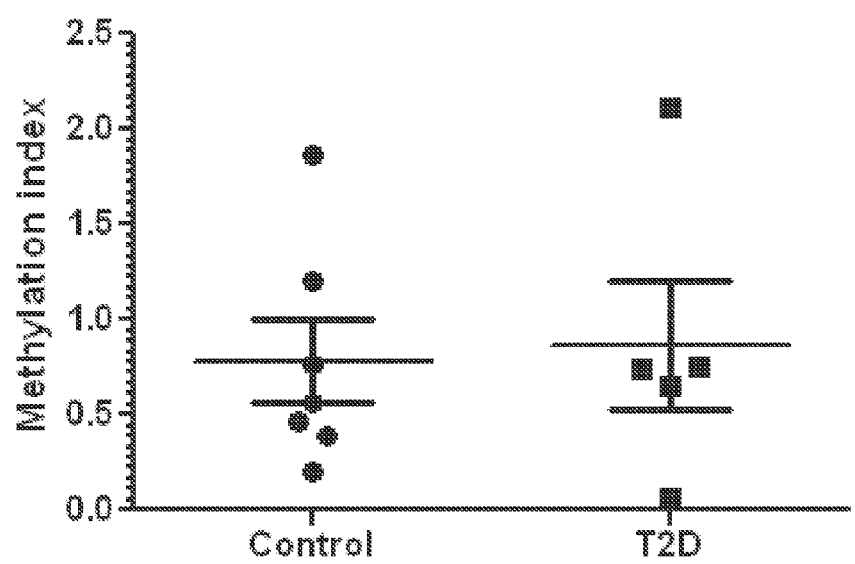
FIG. 3C shows that nested PCR using primers generally according to Akirav (2011) fail to reveal a significant increase in demethylated β cell DNA in the serum of the patients with long-standing Type 2 diabetes.

The present method extends the use of demethylated β cell derived DNA as a biomarker of Type 2 diabetes. The ability of the present assay to detect β cell loss in Type 2 diabetes is clearly shown by the experimental results obtained with the use of the present method. FIG. 3A shows impaired glucose levels in patients with long-standing Type 2 diabetes. FIG. 3B shows the increase in demethylated β cell DNA (i.e., increase in methylation index) in the serum of these patients, revealed as a significant difference (p=0.0286) from control by the use of the present probe technology. Similar results are also observed in animal models of Type 2 diabetes. FIG. 3C shows the use of primers from Akirav et al. (2011) to analyze the same sample set, and failed to detect any significant difference (p=0.87) in methylation index between control and T2D patients.

For PCR according to Akirav et al., (2011), shown in FIG. 3C was conducted for 40 cycles, with a melting temperature of 54° C., using primers as follows:

```
Forward primer:
                                   SEQ ID NO: 007
TTAGGGGTTTTAAGGTAGGGTATTTGGT Reverse primer:
                                   SEQ ID NO: 008
ACCAAAAACAACAATAAACAATTAACTCACCCTACAA
```

The second step real-time methylation-specific nested PCR according to Akirav et al. (2011) was conducted with 50 cycles of amplification, and a melting temperature of 64° C., with the following primers:

```
Methylated forward primer:
                                   SEQ ID NO: 009
GTGGATGCGTTTTTTGTTTTTGTTGGC
```

```
Methylated reverse primer:
                                   SEQ ID NO: 010
CACCCTACAAATCCTCTACCTCCCG Demethylated forward primer:
                                   SEQ ID NO. 011
TTGTGGATGTGTTTTTTGTTTTTGTTGGT Demethylated reverse primer:
                                   SEQ ID NO: 012
CACCCTACAAATCCTCTACCTCCCA
```

Figure 4A:
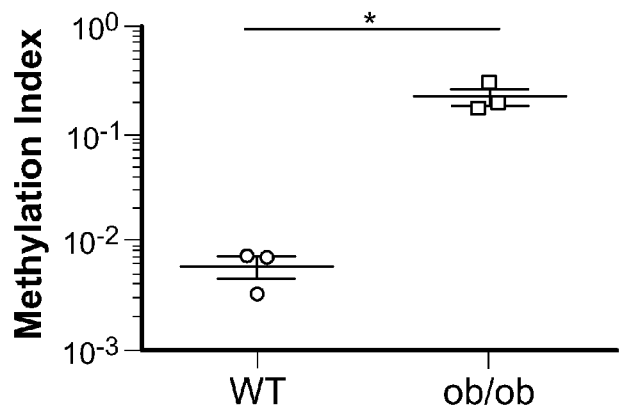
FIG. 4A shows the ability of the assay used in the present method to detect elevated demethylated DNA levels in the ob/ob leptin deficient mouse model of Type 2 diabetes.
Figure 4B:
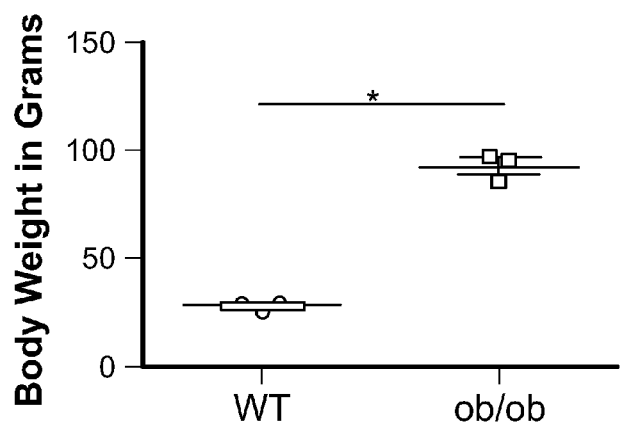
FIG. 4B correlates the levels shown in FIG. 4A with elevated body weight.
Figure 4C:
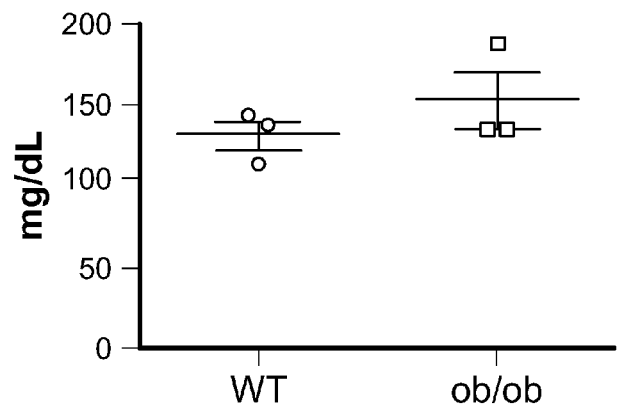
FIG. 4C correlates the levels shown in FIG. 4A with increased glucose levels.

FIG. 4A shows the ability of to detect elevated demethylated DNA levels in the ob/ob leptin deficient mouse model of type 2 diabetes. These levels were correlated with elevated body weight, shown in FIG. 4B, and increased glucose levels, shown in FIG. 4C.

Although the present invention has been described in relation to particular embodiments thereof, many other variations and modifications and other uses will become apparent to those skilled in the art. It is preferred, therefore, that the present invention be limited not by the specific disclosure herein, but only by the appended claim.

REFERENCES

Each of which is Expressly Incorporated Herein by Reference

1. Akirav E, Kushner J A, Herold K C (2008) β-cell mass and type 1 diabetes: Going, going, gone? Diabetes 57:2883-2888.
2. Bluestone J A, Herold K, Eisenbarth G (2010) Genetics, pathogenesis and clinical interventions in type 1 diabetes. Nature 464:1293-1300.
3. Waldron-Lynch F, Herold K C (2009) Advances in type 1 diabetes therapeutics: Immunomodulation and β-cell salvage. Endocrinol Metab Clin North Am 38:303-317.
4. Bougneres P F, et al. (1988) Factors associated with early remission of type I diabetes in children treated with cyclosporine. N Engl J Med 318:663-670.
5. Keymeulen B, et al. (2005) Insulin needs after CD3-antibody therapy in new-onset type 1 diabetes. N Engl J Med 352:2598-2608.
6. Ludvigsson J, Heding L (1982) Abnormal proinsulin/C-peptide ratio in juvenile diabetes. Acta Diabetol Lat 19:351-358.
7. Snorgaard O, Lassen L H, Binder C (1992) Homogeneity in pattern of decline of β-cell function in IDDM: Prospective study of 204 consecutive cases followed for 7.4 yr. Diabetes Care 15:1009-1013.
8. Greenbaum C J, et al.; Type 1 Diabetes Trial Net Research Group; European C-Peptide Trial Study Group (2008) Mixed-meal tolerance test versus glucagon stimulation test for the assessment of β-cell function in therapeutic trials in type 1 diabetes. Diabetes Care 31:1966-1971.
9. Steele C, et al. (2004) Insulin secretion in type 1 diabetes. Diabetes 53:426-433.
10. Erlich H, et al.; Type 1 Diabetes Genetics Consortium (2008) HLA DR-DQ haplotypes and genotypes and type 1 diabetes risk: Analysis of the Type 1 Diabetes Genetics Consortium families. Diabetes 57:1084-1092.
11. Hagopian W A, et al. (1995) Glutamate decarboxylase, insulin, and islet cell antibodies and HLA typing to detect diabetes in a general population-based study of Swedish children. J Clin Invest 95:1505-1511.

12. Verge C F, et al. (1996) Prediction of type I diabetes in first-degree relatives using a combination of insulin, GAD, and ICA512bdc/IA-2 autoantibodies. Diabetes 45: 926-933.
13. Shen J, Sosenko J, Skyler J S, Herold K C (2008) Prevention of type 1 diabetes: The time has come. Nat Clin Pract Endocrinol Metab 4:334-343.
14. Sosenko J M, et al.; Diabetes Prevention Trial Type 1 Study Group (2007) Increasing the accuracy of oral glucose tolerance testing and extending its application to individuals with normal glucose tolerance for the prediction of type 1 diabetes: The Diabetes Prevention Trial Type 1. Diabetes Care 30:38-42.
15. Medarova Z, Tsai S, Evgenov N, Santamaria P, Moore A (2008) In vivo imaging of a diabetogenic CD8+ T cell response during type 1 diabetes progression. Magn Reson Med 59:712-720.
16. Klose R J, Bird A P (2006) Genomic DNA methylation: The mark and its mediators. Trends Biochem Sci 31:89-97.
17. Bartke T, et al. (2010) Nucleosome-interacting proteins regulated by DNA and histone methylation. Cell 143:470-484.
18. Wang G G, Allis C D, Chi P (2007) Chromatin remodeling and cancer, part II: ATP-dependent chromatin remodeling. Trends Mol Med 13:373-380.
19. Miranda T B, Jones P A (2007) DNA methylation: The nuts and bolts of repression. J Cell Physiol 213:384-390.
20. Grady W M, Rajput A, Lutterbaugh J D, Markowitz S D (2001) Detection of aberrantly methylated hMLH1 promoter DNA in the serum of patients with microsatellite un-stable colon cancer. Cancer Res 61:900-902.
21. Wallner M, et al. (2006) Methylation of serum DNA is an independent prognostic marker in colorectal cancer. Clin Cancer Res 12:7347-7352.
22. Müller H M, et al. (2003) DNA methylation in serum of breast cancer patients: An independent prognostic marker. Cancer Res 63:7641-7645.
23. Poitout V, et al. (1995) Morphological and functional characterization of β TC-6 cells: An insulin-secreting cell line derived from transgenic mice. Diabetes 44:306-313.
24. Sherry N A, et al. (2006) Effects of autoimmunity and immune therapy on β-cell turnover in type 1 diabetes. Diabetes 55:3238-3245.
25. Jayaraman S (2011) Assessment of beta cell viability. Curr Protoc Cytom 55:6.27.1-6.27.16.
26. Kuroda A, et al. (2009) Insulin gene expression is regulated by DNA methylation. PLoS ONE 4:e6953.
27. Giddings S J, King C D, Harman K W, Flood J F, Carnaghi L R (1994) Allele-specific inactivation of insulin 1 and 2 in the mouse yolk sac indicates imprinting. Nat Genet 6:310-313.
28. Leiter E H, et al. (2007) Unexpected functional consequences of xenogeneic transgene expression in β-cells of NOD mice. Diabetes Obes Metab 9(Suppl 2):14-22.
29. Trudeau J D, et al. (2000) Neonatal β-cell apoptosis: A trigger for autoimmune diabetes? Diabetes 49:1-7.
30. Fujimoto K, et al. (2010) Loss of Nix in Pdx1-deficient mice prevents apoptotic and necrotic β cell death and diabetes. J Clin Invest 120:4031-4039.
31. Basadonna G, Montorsi F, Kakizaki K, Merrell R C (1988) Cyclosporin A and islet function. Am J Surg 156: 191-193.
32. Berney T, et al. (2006) Detection of insulin mRNA in the peripheral blood after human islet transplantation predicts deterioration of metabolic control. Am J Transplant 6:1704-1711.
33. Best C H, Haist R E, Ridout J H (1939) Diet and the insulin content of pancreas. J Physiol 97:107-119.
34. Collins T J (2007) ImageJ for microscopy. Biotechniques 43(Suppl 1):25-30.
35. Irina Botezatu, Ol'ga Serdyuk, Galina Potapova, Valery Shelepov, Raisa Alechina, Yuriy Molyaka, Vitaliy Anan'ev, Igor Bazin, August Garin, Mehti Narimanov, Vasiliy Knysh, Hovsep Melkonyan, Samuil Umansky, and Anatoly Lichtenstein (2000) "Genetic Analysis of DNA Excreted in Urine: A New Approach for Detecting Specific Genomic DNA Sequences from Cells Dying in an Organism", Clinical Chemistry 46:8 1078-1084.
36. Umansky, S. R., et al. (1982) "In vivo DNA degradation of thymocytes of gamma-irradiated or hydrocortisone-treated rats"; Biochim. Biophys. Acta 655:9-17.
37. Lichtenstein, A. V., et al. (2001), "Circulating nucleic acids and apoptosis"; Ann NY Acad Sci, 945:239-249.

What is claimed is:

1. A method for monitoring beta cell death, comprising:
   extracting and purifying DNA from a body fluid of an animal or human;
   treating the extracted purified DNA with bisulfite to convert demethylated cytosine to uracil while sparing the methylated cytosines;
   amplifying the bisulfite-treated DNA using polymerase chain reaction;
   purifying the amplified bisulfite-treated DNA;
   providing methylation-status specific probes configured to measure, in a quantitative methylation-status sensitive probe hybridization reaction, demethylated insulin DNA of β cell origin and methylated insulin DNA of non-β cell origin, comprising:
   a) at least one probe for detection of methylated insulin DNA of non-β cell origin selected from the group consisting of ACCTCCCGACGAATCT SEQ ID NO: 003 and TACCTCTCGTCGAATCT SEQ ID NO: 004; and
   b) at least one probe for detection of demethylated insulin DNA of β cell origin selected from the group consisting of ACCTCCCAACAAATCT SEQ ID NO: 005 and TACCTCCCATCAAATCT SEQ ID NO: 006;
   performing the quantitative methylation sensitive probe hybridization reaction on the purified bisulfite-treated DNA using the methylation-status specific probes; and
   quantitatively analyzing relative amounts of methylated insulin DNA and demethylated insulin DNA.

2. The method according to claim 1, wherein the polymerase chain reaction is conducted using a forward primer: GTGCGGTTTATATTTGGTGGAAGTT SEQ ID NO: 001 and a reverse primer: ACAACAATAAACAATTAACTCAC-CCTACAA SEQ ID NO: 002.

3. The method according to claim 1, wherein the methylation-status specific probes are conjugated to a fluorophore.

4. The method according to claim 3, wherein the fluorophore is 6-carboxy fluorescein.

5. The method according to claim 3, wherein the fluorophore is tetrachlorofluorescein.

6. The method according to claim 3, wherein each methylation-status specific probe comprises a quencher.

7. The method according to claim 6, wherein the quencher is tetramethylrhodamine.

8. The method according to claim 4, wherein the methylation-sensitive probe hybridization reaction comprises a quantitative release of a fluorophore from a probe bound to the purified bisulfite-treated DNA and wherein the quantitative analysis of the relative amounts of methylated insulin DNA and demethylated insulin DNA comprises monitoring the release of the fluorophore from the probe bound to the purified bisulfite-treated DNA.

9. The method according to claim 1, wherein the body fluid is derived from blood, wherein the quantitative analysis statistically distinguishes between blood from a patient having type II diabetes and blood from a patient without diabetes.

10. A method for monitoring cell death of a cell type having at least one DNA portion that has a unique DNA CpG methylation-pattern as compared to other cells, the at least one DNA portion that has a unique DNA CpG methylation-pattern being released into body fluids upon cell death of cells of the cell type, comprising:
  extracting and purifying DNA that comprises the DNA portion;
  treating the extracted purified DNA with bisulfite to convert cytosine to uracil while sparing the CpG methylated cytosines;
  amplifying a region of the bisulfite-treated DNA that comprises the DNA portion by polymerase chain reaction using DNA CpG methylation-pattern independent primers;
  providing DNA CpG methylation-pattern specific probes configured to measure, in a quantitative DNA CpG methylation sensitive probe hybridization reaction, demethylated insulin DNA of β cell origin and CpG methylated insulin DNA of non-β cell origin, wherein the DNA CpG methylation pattern-specific probes comprise:
  a) at least one probe for detection of methylated insulin DNA of non-β cell origin selected from the group consisting of ACCTCCCGACGAATCT SEQ ID NO: 003 and TACCTCTCGTCGAATCT SEQ ID NO: 004; and
  b) at least one probe for detection of demethylated insulin DNA of β cell origin selected from the group consisting of ACCTCCCAACAAATCT SEQ ID NO: 005 and TACCTCCCATCAAATCT SEQ ID NO: 006;
  performing a quantitative methylation sensitive probe hybridization reaction on the purified bisulfite-treated DNA using the DNA CpG methylation-pattern specific probes, wherein the probe for detection of demethylated insulin DNA of β cell origin measures the amount of the DNA portion having a unique DNA CpG methylation-pattern and the probe for detection of methylated insulin DNA of non-β cell origin measures the amount of the DNA portion lacking a unique DNA CpG methylation pattern;
  quantitatively analyzing the relative amount of DNA portion having the unique DNA CpG methylation-pattern to DNA portion lacking the unique DNA CpG methylation pattern.

11. The method according to claim 10, wherein the DNA portion having the unique DNA CpG methylation-pattern comprises an insulin gene from a pancreatic beta cell.

12. The method according to claim 10, wherein the polymerase chain reaction is conducted using a DNA CpG methylation pattern-independent forward primer: GTGCGGTTTATATTTGGTGGAAGTT SEQ ID NO: 001 and a DNA CpG methylation pattern-independent reverse primer: ACAACAATAAACAATTAACTCACCCTACAA SEQ ID NO: 002.

13. The method according to claim 10, wherein the DNA CpG methylation-pattern specific probes are conjugated to a fluorophore and a quencher.

14. The method according to claim 13, wherein the quantitative methylation sensitive probe hybridization reaction comprises a quantitative release of the fluorophore from DNA CpG methylation-pattern specific probes and wherein the quantitative analysis of the relative amounts of the DNA portion having the unique DNA CpG methylation-pattern to the DNA portion lacking the unique DNA CpG methylation-pattern comprises monitoring the release of the fluorophore from the DNA CpG methylation-pattern specific probes bound to the purified bisulfite-treated DNA.

15. The method according to claim 13, wherein in the methylation sensitive probe hybridization reaction, the binding of the DNA CpG methylation-pattern specific probes to a respective target sequence of the purified bisulfite-treated DNA causes a conformational change and alters the interaction of the fluorophore and quencher conjugated to said probes.

16. The method according to claim 10, wherein the body fluid is derived from blood, the cell type having at least one DNA portion that has a unique DNA CpG methylation-pattern is a β cell, and the quantitative analysis statistically distinguishes between blood of a patient having type II diabetes and blood of a patient without diabetes.

17. A method for monitoring beta cell death, comprising:
  extracting and purifying genomic DNA from a body fluid of an animal or human, wherein the genomic DNA comprises at least a portion of a gene that is predominantly expressed by β cells and that contains a CpG methylation site;
  treating the genomic DNA with bisulfite;
  performing a polymerase chain reaction (PCR) with primers that flank a region of the genomic DNA that comprises the CpG methylation site;
  purifying the PCR products;
  melting the PCR products into single strands;
  providing a first oligonucleotide probe capable of hybridizing with a target sequence that comprises a site corresponding to a bisulfite-converted CpG site and providing a second oligonucleotide probe capable of hybridizing with a target sequence that comprises a site corresponding to a bisulfite-nonconverted CpG site,
  wherein the first and second oligonucleotide probes each comprise a non-FRET label pair consisting of a fluorophore and a quencher,
  and wherein interaction of the first oligonucleotide probe or the second oligonucleotide probe with its respective target sequence causes a change from a first conformation to a second conformation, thereby changing the distance between the fluorophore and quencher of said label pair, and wherein in only one conformation do the fluorophore and quencher interact sufficiently to quench the fluorescence of the fluorophore by a predetermined amount;
  hybridizing the single stranded PCR products with the first and second oligonucleotide probes,
  wherein the first oligonucleotide probe is SEQ ID NO: 003 or SEQ ID NO: 004 and the second oligonucleotide probe is SEQ ID NO: 005 or SEQ ID NO: 006;
  quantitatively measuring fluorescent signals emitted by the first oligonucleotide probe and emitted by the second oligonucleotide probe; and
  reporting a quantitative relationship of the fluorescent signal emitted by the first oligonucleotide probe and the second oligonucleotide probe, indicative of the relative amount of β cell-derived DNA versus non-β cell-derived DNA.

18. The method according to claim 17, wherein the primers used for the PCR are SEQ ID NO: 001 and SEQ ID NO: 002 respectively.

19. The method according to claim 17, wherein the fluorophore is 6-carboxy fluorescein or tetrachlorofluorescein and the quencher is tetramethylrhodamine.

20. The method according to claim 17, wherein the body fluid is derived from blood of a patient, wherein the relative amount of β cell-derived DNA versus non-β cell-derived DNA is capable of statistically distinguishing between blood from a patient having type II diabetes and blood from a normal patient.

21. A kit for detecting β cell-derived demethylated genomic DNA in a biological sample, wherein the kit comprises:
PCR primers that flank a portion of a gene that contains a target sequence that is selectively demethylated in β cells and contains at least one CpG methylation site;
a first oligonucleotide probe capable of hybridizing with the target sequence from β-cells on a PCR amplification product of bisulfite treated nucleic acids, wherein the target sequence contains at least one bisulfite-converted CpG methylation site of the portion of the gene; and
a second oligonucleotide probe capable of hybridizing with the target sequence from non-β-cells on a PCR amplification product of bisulfite treated nucleic acids, wherein the target sequence contains at least one bisulfite-nonconverted CpG methylation site of the portion of the gene,
wherein the first oligonucleotide probe comprises a fluorophore and is selected from the group consisting of ACCTCCCGACGAATCT SEQ ID NO: 003 and TACCTCTCGTCGAATCT SEQ ID NO: 004; and
wherein the second oligonucleotide probe comprises a fluorophore and is selected from the group consisting of ACCTCCCAACAAATCT SEQ ID NO: 005 and TACCTCCCATCAAATCT SEQ ID NO: 006.

22. The kit according to claim 21, wherein the first and second oligonucleotide probes each further comprise a quencher, and wherein in a binding interaction of the first oligonucleotide probe with the bisulfite converted CpG methylation site of the target sequence, and the second oligonucleotide probe with the bisulfite non-converted CpG methylation site of the target sequence, a change from a first conformation to a second conformation occurs, thereby changing an interaction between the fluorophore and quencher of the respective probe, and wherein in only one conformation of the first and second conformations do the fluorophore and quencher interact sufficiently to quench the fluorescence of the fluorophore by at least 25 percent.

23. A method for monitoring beta cell death, comprising:
extracting and purifying DNA from a body fluid of an animal or human;
treating the extracted purified DNA with bisulfite to convert demethylated cytosine to uracil while sparing the methylated cytosines;
amplifying the bisulfite-treated DNA using polymerase chain reaction using insulin DNA-specific primers;
purifying the amplified bisulfite-treated DNA;
providing at least one of methylation-status specific probe configured to measure, in a quantitative methylation-status sensitive probe hybridization reaction, methylated insulin DNA of non-β cell origin, wherein the probe for detection of methylated insulin DNA of non-β cell origin is selected from the group consisting of ACCTCCCGACGAATCT SEQ ID NO: 003 and TACCTCTCGTCGAATCT SEQ ID NO: 004; and
providing at least one of methylation-status specific probe configured to measure, in a quantitative methylation-status sensitive probe hybridization reaction, demethylated insulin DNA of β cell origin, wherein the probe for detection of the demethylated insulin DNA of β cell origin is selected from the group consisting of ACCTCCCAACAAATCT SEQ ID NO: 005 and TACCTCCCATCAAATCT SEQ ID NO: 006;
performing the quantitative methylation sensitive probe hybridization reaction on the purified bisulfite-treated DNA using the methylation-status specific probes; and
quantitatively analyzing relative amounts of methylated insulin DNA and demethylated insulin DNA.

* * * * *

SEQUENCE LISTING

```
<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Forward PCR Primer for insulin gene

<400> SEQUENCE: 1
gtgcggttta tatttggtgg aagtt                                          25

<210> SEQ ID NO 2
<211> LENGTH: 30
<212> TYPE: DNA
<213> ORGANISM: Artificial Sequence
<220> FEATURE:
<223> OTHER INFORMATION: Reverse PCR primer for insulin gene

<400> SEQUENCE: 2
acaacaataa acaattaact caccctacaa                                     30
```

<210> SEQ ID NO 3
<211> LENGTH: 16
<212> TYPE: DNA
<213> ORGANISM: Artificial Sequence
<220> FEATURE:
<223> OTHER INFORMATION: Probe for the detection of methylated non-beta
      cell insulin DNA

<400> SEQUENCE: 3
acctcccgac gaatct                                                           16

<210> SEQ ID NO 4
<211> LENGTH: 17
<212> TYPE: DNA
<213> ORGANISM: Artificial Sequence
<220> FEATURE:
<223> OTHER INFORMATION: Probe for the detection of methylated non-beta
      cell insulin DNA

<400> SEQUENCE: 4
tacctctcgt cgaatct                                                          17

<210> SEQ ID NO 5
<211> LENGTH: 16
<212> TYPE: DNA
<213> ORGANISM: Artificial Sequence
<220> FEATURE:
<223> OTHER INFORMATION: Probe for the detection of demethylated beta
      cell insulin DNA

<400> SEQUENCE: 5
acctcccaac aaatct                                                           16

<210> SEQ ID NO 6
<211> LENGTH: 17
<212> TYPE: DNA
<213> ORGANISM: Artificial Sequence
<220> FEATURE:
<223> OTHER INFORMATION: probe for the detection of demethylated beta
      cell insulin dna

<400> SEQUENCE: 6
tacctcccat caaatct                                                          17

<210> SEQ ID NO 7
<211> LENGTH: 28
<212> TYPE: DNA
<213> ORGANISM: Artificial Sequence
<220> FEATURE:
<223> OTHER INFORMATION: Outer Forward PCR primer for nested PCR
      according to Akirav et al. (2011)

<400> SEQUENCE: 7
ttagggtttt taaggtaggg tatttggt                                              28

<210> SEQ ID NO 8
<211> LENGTH: 37
<212> TYPE: DNA
<213> ORGANISM: Artificial Sequence
<220> FEATURE:
<223> OTHER INFORMATION: Outer Reverse PCR primer for nested PCR
      according to Akirav et al. (2011)

<400> SEQUENCE: 8
accaaaaaca acaataaaca attaactcac cctacaa                                    37

```
<210> SEQ ID NO 9
<211> LENGTH: 27
<212> TYPE: DNA
<213> ORGANISM: Artificial Sequence
<220> FEATURE:
<223> OTHER INFORMATION: Inner Methylated Forward PCR primer for nested
      PCR according to Akirav et al. (2011)

<400> SEQUENCE: 9
gtggatgcgt tttttgtttt tgttggc                                        27

<210> SEQ ID NO 10
<211> LENGTH: 25
<212> TYPE: DNA
<213> ORGANISM: Artificial Sequence
<220> FEATURE:
<223> OTHER INFORMATION: Inner Methylated Reverse PCR primer for nested
      PCR according to Akirav et al. (2011)

<400> SEQUENCE: 10
caccctacaa atcctctacc tcccg                                          25

<210> SEQ ID NO 11
<211> LENGTH: 29
<212> TYPE: DNA
<213> ORGANISM: Artificial Sequence
<220> FEATURE:
<223> OTHER INFORMATION: Inner Demethylated Forward PCR primer for
      nested PCR according to Akirav et al. (2011)

<400> SEQUENCE: 11
ttgtggatgt gtttttttgtt tttgttggt                                     29

<210> SEQ ID NO 12
<211> LENGTH: 25
<212> TYPE: DNA
<213> ORGANISM: Artificial Sequence
<220> FEATURE:
<223> OTHER INFORMATION: Inner Demethylated Reverse PCR primer for
      nested PCR according to Akirav et al. (2011)

<400> SEQUENCE: 12
caccctacaa atcctctacc tccca                                          25
```